(12) United States Patent
Xiong et al.

(10) Patent No.: US 7,271,891 B1
(45) Date of Patent: Sep. 18, 2007

(54) APPARATUS AND METHODS FOR PROVIDING SELECTIVE DEFECT SENSITIVITY

(75) Inventors: Yalin Xiong, Union City, CA (US); Zain K. Saidin, San Mateo, CA (US); Sterling G. Watson, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 1 day.

(21) Appl. No.: 10/928,585

(22) Filed: Aug. 26, 2004

Related U.S. Application Data (60) Provisional application No. 60/499,225, filed on Aug. 29, 2003.

(51) Int. Cl.
*G01N 21/88* (2006.01)
*G06K 9/00* (2006.01)

(52) U.S. Cl. .................. 356/237.4; 356/327.5; 356/237.1; 356/394; 250/559.39; 382/145

(58) Field of Classification Search .. 356/237.1–237.5, 356/390–394; 382/1, 8, 30, 34, 145; 250/559.39, 250/559.41, 559.46, 548; 716/19
See application file for complete search history.

(56) References Cited

U.S. PATENT DOCUMENTS

| | | | | |
|---|---|---|---|---|
| 4,641,353 A * | 2/1987 | Kobayashi | ................ | 382/144 |
| 4,718,767 A * | 1/1988 | Hazama | .................... | 356/389 |
| 5,767,974 A * | 6/1998 | Higashiguchi et al. | ...... | 356/394 |
| 5,822,055 A * | 10/1998 | Tsai et al. | ................ | 356/237.1 |
| 5,850,467 A * | 12/1998 | Matsui et al. | ................ | 382/145 |
| 5,969,807 A * | 10/1999 | Levinson et al. | ........... | 356/124 |
| 5,995,219 A * | 11/1999 | Tabata | ..................... | 356/237.5 |
| 6,091,845 A * | 7/2000 | Pierrat et al. | ............... | 382/144 |
| 6,169,603 B1 * | 1/2001 | Takayama | ................... | 356/500 |
| 6,285,783 B1 * | 9/2001 | Isomura et al. | ............. | 382/147 |
| 6,466,314 B1 * | 10/2002 | Lehman | ................... | 356/237.1 |
| 6,516,085 B1 * | 2/2003 | Wiley et al. | ................ | 382/144 |
| 6,578,188 B1 * | 6/2003 | Pang et al. | ................... | 716/19 |
| 6,645,676 B1 * | 11/2003 | Miyasaka | ...................... | 430/5 |

* cited by examiner

*Primary Examiner*—Sang H. Nguyen
(74) *Attorney, Agent, or Firm*—Beyer Weaver LLP (57) ABSTRACT

Disclosed are techniques and apparatus for accounting for differing levels of defect susceptibility in different pattern areas of a reticle in an inspection of such reticle or in inspection of a semiconductor device fabricated from such reticle. In general terms, two or more areas of a reticle are analyzed to quantify each area's susceptibility to defects on the final semiconductor product. That is, each reticle area is analyzed and given a quantified defect susceptibility value, such as a MEEF (mask error enhancement factor) value. Such analysis includes analysis of an image that is estimated to result from the lithography tool which is to be utilized to expose semiconductor devices with the reticle. The defect susceptibility value generally depends on the reticle area's density and whether the correspond area of the estimated lithography image has intensity values which are proximate to an exposure threshold for a particular resist material to be used on the final semiconductor device. The quantified defect susceptibility for each reticle area is then used to selectively set the inspection sensitivity for each reticle area or its corresponding semiconductor device region. The reticle and/or resulting semiconductor device may then be inspected based on the selected sensitivity levels for the different areas of the sample under test.

33 Claims, 6 Drawing Sheets

APPARATUS AND METHODS FOR PROVIDING SELECTIVE DEFECT SENSITIVITY

CROSS REFERENCE TO RELATED PATENT APPLICATION

This application claims priority of U.S. Provisional Patent Application No. 60/499,225, entitled APPARATUS AND METHODS FOR PROVIDING SELECTIVE DEFECT SENSITIVITY, filed 29 Aug. 2003 by Yalin Xiong, et al., which application is incorporated herein by reference in its entirety for all purposes.

BACKGROUND OF THE INVENTION

The present invention relates generally to the field of semiconductor inspection. More specifically, it relates to techniques for improving the sensitivity of defect detection on semiconductor samples, such as reticles and semiconductor devices.

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the devices are ever increasingly sensitive to defects. That is, defects which cause faults in the device are becoming increasingly smaller. The device must be fault free prior to shipment of the device to the end users or customers.

An integrated circuit is typically fabricated from a plurality of reticles. Generation of reticles and subsequent optical inspection of such reticles have become standard steps in the production of semiconductors. Initially, circuit designers provide circuit pattern data, which describes a particular integrated circuit (IC) design, to a reticle production system, or reticle writer. The circuit pattern data is typically in the form of a representational layout of the physical layers of the fabricated IC device. The representational layout includes a representational layer for each physical layer of the IC device (e.g., gate oxide, polysilicon, metallization, etc.), wherein each representational layer is composed of a plurality of polygons that define a layer's patterning of the particular IC device.

The reticle writer uses the circuit pattern data to write (e.g., typically, an electron beam writer or laser scanner is used to expose a reticle pattern) a plurality of reticles that will later be used to fabricate the particular IC design. A reticle inspection system may then inspect the reticle for defects that may have occurred during the production of the reticles.

A reticle or photomask is an optical element containing at least transparent and opaque regions, and sometimes semi-transparent and phase shifting regions, which together define the pattern of coplanar features in an electronic device such as an integrated circuit. Reticles are used during photolithography to define specified regions of a semiconductor wafer for etching, ion implantation, or other fabrication process. For many modern integrated circuit designs, an optical reticle's features are between about 1 and about 5 times larger than the corresponding features on the wafer (e.g., fir laser lithography systems). For other exposure systems (e.g., x-ray, e-beam, and extreme ultraviolet), a similar range of reduction ratios also apply.

After fabrication of each reticle or group of reticles, each reticle is typically inspected by illuminating it with light emanating from a controlled illuminator. A test image of a portion of the reticle is constructed based on the portion of the light reflected, transmitted, or otherwise directed to a light sensor. Such inspection techniques and apparatus are well known in the art and are embodied in various commercial products such as many of those available from KLA-Tencor Corporation of San Jose, Calif.

During a conventional inspection process, the test image of the reticle is typically compared to a baseline image. Typically, the baseline image is either generated from the circuit pattern data or from an adjacent die on the reticle itself. Either way, the test image features are analyzed and compared with corresponding features of the baseline image. That is, an edge position within the test image is subtracted from a corresponding edge position within the baseline image to calculate a difference value. Each difference value is then compared with a predetermined threshold value. If the test image feature varies from the baseline feature by more than the predetermined threshold, a defect is defined and an error is reported.

Since defects on a reticle may be reproduced or printed on the resulting integrated circuit pattern, it is important to detect defects in each reticle prior to using the reticle to manufacturing integrated circuits. If defects are found in the reticle, the reticle can then be repaired or discarded before the reticle can produce faulty semiconductor devices. Unfortunately, all discrepancies on a reticle do not have a same effect on the corresponding integrated circuit pattern. For instance, not all reticle discrepancies are printed to the same degree on the wafer the same during the photolithography process. Additionally, some reticle discrepancies cause faults in the semiconductor device, while others do not. Whether the reticle discrepancy results in a printable error or fault on the integrated circuit depends on defect characteristics, such as size of the reticle discrepancy and characteristics of patterns which are proximate to the defect, such as density.

As described above, typical inspection processes detect defects on the reticle by comparing two areas on one or more reticles which are designed to be identical. When the difference is higher than a predetermined threshold, the difference is classified as a defect. Each difference detected between the two areas has the potential of resulting in a printable defect. Conversely, some of the detected defects will have no effect on the resulting integrated circuit. Although the threshold is typically set to capture defects having a size that will likely result in an actual integrated circuit defect, this technique sometimes fails to capture small defects that fall within densely packed active regions and, accordingly, tend to result in faults. Additionally, using a fixed threshold value does not account for different reticle patterns having varying degree of susceptibility to defects. That is, inspection of the reticle does not consider that one reticle pattern area will likely be significantly more susceptible to defects than a different reticle pattern area.

Accordingly, there is a need for improved inspection techniques for more accurately and reliably detecting defects in reticles, as well as detecting defects in the resulting integrated circuit. Additionally, it would be desirable to have techniques for accounting for the differences in defect susceptibility inherent in different reticle patterns

SUMMARY OF THE INVENTION

Accordingly, mechanisms are provided for accounting for differing levels of defect susceptibility in different pattern areas of a reticle in an inspection of such reticle or in inspection of a semiconductor device fabricated from such reticle. In general terms, two or more areas of a reticle are analyzed to quantify each area's susceptibility to defects on the final semiconductor product. That is, each reticle area is analyzed and given a quantified defect susceptibility value, such as a MEEF (mask error enhancement factor) value. Such analysis includes analysis of an image that is estimated to result from the lithography tool which is to be utilized to expose semiconductor devices with the reticle. The defect susceptibility value generally depends on the reticle area's density and whether the correspond area of the estimated lithography image has intensity values which are proximate to an exposure threshold for a particular resist material to be used on the final semiconductor device. The quantified defect susceptibility for each reticle area is then used to selectively set the inspection sensitivity for each reticle area or its corresponding semiconductor device region. The reticle and/or resulting semiconductor device may then be inspected based on the selected sensitivity levels for the different areas of the sample under test.

In one embodiment, a method of providing selective defect sensitivity in inspection of semiconductor specimens. Initially, in operation (a) an image of a target portion of a specimen is provided. The specimen is typically a reticle. The target portion contains a number of different pattern portions. In operation (b), these pattern portions of the specimen are analyzed to thereby determine a characteristic of defect susceptibility for each pattern portion. In operation (c), a sensitivity level for inspection of each pattern portion of the specimen is then determined so that it corresponds to the determined defect susceptibility characteristic of such each pattern portion. In one further aspect, each portion of the specimen (e.g., reticle) is then inspected using the determined sensitivity level for such specimen portion. In another aspect, a plurality of wafer portions fabricating with corresponding pattern portions of the reticle are inspected. Inspection of each wafer portion is based on the determined defect susceptibility characteristic for the corresponding pattern portion of the reticle.

In a specific implementation, the determination of the sensitivity level includes selecting a threshold for each pattern portion based on the determined defect susceptibility characteristic of such pattern portion. Thus, each portion of the specimen may then be inspected using the selected threshold for such specimen portion.

In one aspect, operations (a) through (c) are performed for both a target portion of the specimen and a baseline portion of the specimen. The target portion is designed to be substantially identical to the baseline portion of the specimen, and the sensitivity level for the inspection is based on both the determined defect susceptibility for the target portion and the reference portion.

In one implementation, the operation of analyzing the pattern portions of the specimen includes (i) simulating an approximation of a lithography image which would be produced by a lithography tool which is to be used to expose a semiconductor device with the reticle; (ii) simulating resist development results using the approximation of the lithography image; and (iii) generating a defect susceptibility map for the reticle based on the simulated resist development results. In a specific aspect, the approximation of the lithography image is simulated by convoluting a low pass filter function with the image of the target portion of the specimen. In a further aspect, the filter function also incorporates at least some of the differences between the lithography tool and an inspection tool which is to be used to inspect the reticle or a semiconductor device fabricated from such reticle. Preferably, the filter function is further based on at least a portion of a plurality of configuration parameters associated with the lithography tool. In one example, the defect susceptibility map is in the form of a pseudo Mask Error Enhancement Factor (MEEF) map, and the sensitivity level for inspection is in the form of threshold map, wherein high MEEF values result in low threshold values and low MEEF values result in high threshold values.

In another aspect, operations (a) through (c) are performed for both a target portion of the specimen and a baseline portion of the specimen, and the target portion is designed to be substantially identical to the baseline portion of the specimen. In a first comparison, the image of the target portion is compared to the image of the baseline portion and it is determined that the target portion has a defect based on the comparison and determined sensitivity levels. In a second comparison, the resist development results obtained from the image of the target portion is compared to the resist development results obtained from the image of the baseline portion and determining that the target portion has a defect based on the second comparison and the determined sensitivity levels.

In a specific implementation, generating the defect susceptibility map is accomplished by combining results from the following rules: 1. when a slope of the simulated resist development results is relatively steep, associating a higher defect susceptibility value to the corresponding reticle portion; 2. when a slope of the simulated resist development results is relatively shallow, associating a lower defect susceptibility value to the corresponding reticle portion; 3. when an intensity value of the simulated resist development results is a relatively far distance from an activation threshold of a resist material which is to be used with the reticle, associating a lower defect susceptibility value to the corresponding reticle portion; and 4. when an intensity value of the simulated resist development results is a relatively short distance from an activation threshold of a resist material which is to be used with the reticle, associating a higher defect susceptibility value to the corresponding reticle portion.

In another aspect, the invention pertains to a computer system operable to provide selective defect sensitivity in inspection of semiconductor specimens. The computer system includes one or more processors and one or more memory configured to perform one or more of the above method operations. In yet another aspect, the invention pertains to a computer program product for providing selective defect sensitivity in inspection of semiconductor specimens. The computer program product includes at least one computer readable medium and computer program instructions stored within the at least one computer readable product configured to perform one or more of the above described inventive procedures.

These and other features and advantages of the present invention will be presented in more detail in the following specification of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Figure 1:
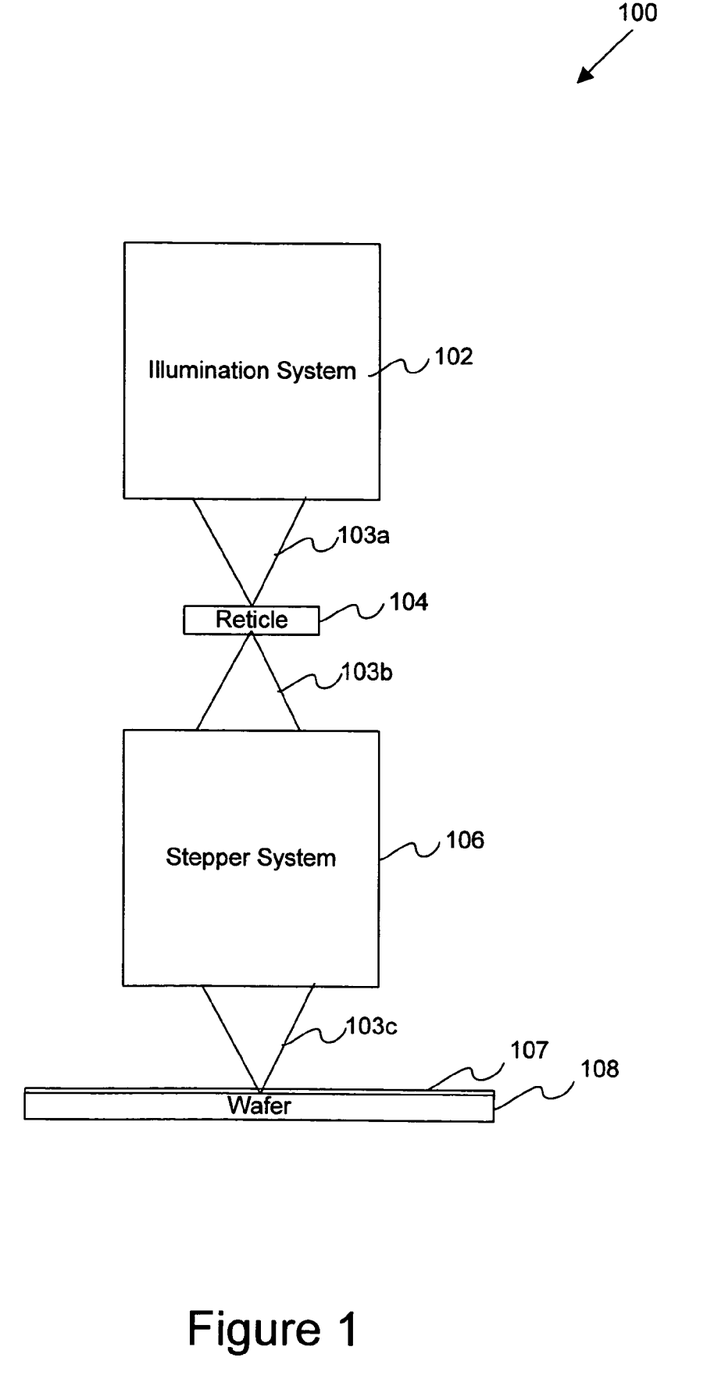
FIG. 1 is a diagrammatic representation of a photolithography system.

FIG. 1 is a diagrammatic representation of a photolithography system. The individual components of the system 100 are not shown to scale so as to better illustrate the working of such a system 100. The photolithography system 100 generally includes an illumination system 102 for outputting beam 103a through reticle 104. The photolithography system may take any suitable form, such as a stepper type system or a stepper scan system. Beam 103a passes through transparent portions of the reticle 104 and then through an lithographic imaging system 106. By way of examples, the beam may be in the form of an optical beam such as a laser or an extreme ultraviolet beam, an electron beam, or an x-ray beam.

Optical reticles are typically made from a transparent medium such as a borosilicate glass or quartz plate on which is deposited an opaque and/or semi-opaque layer of chromium or other suitable material. However, other mask technologies are employed for direct e-beam exposure (e.g., stencil masks), x-ray exposure (e.g., absorber masks), etc. The reticle pattern may be created by a laser or an e-beam direct write technique, for example, both of which are widely used in the art.

Beam 103b is output from reticle 104 into the photolithography system 106. The lithography imaging system 106 generally outputs a beam 103c onto a portion of wafer 108. The output beam 103c exposes the wafer at a particular stage of the processing. After a particular active layer is deposited on the semiconductor wafer 108, a photoresist layer 107 is then deposited on the particular active layer. The beam 103c activates specific portions of the exposed area of the photoresist 107 according to the patterns on reticle 104. The exposed portions of the active layer are then etched away, for example, for positive photoresist (or remain unetched for negative resist) to form a corresponding pattern on the activated layer of the integrated circuit. The exposed portions may alternatively be subjected to ion implantation or any other suitable fabrication step for patterning the exposed layer. The lithography tool 100 is typically configured to sequentially expose different areas of the wafer until the entire wafer is exposed to the output beam 103c.

Figure 2A:
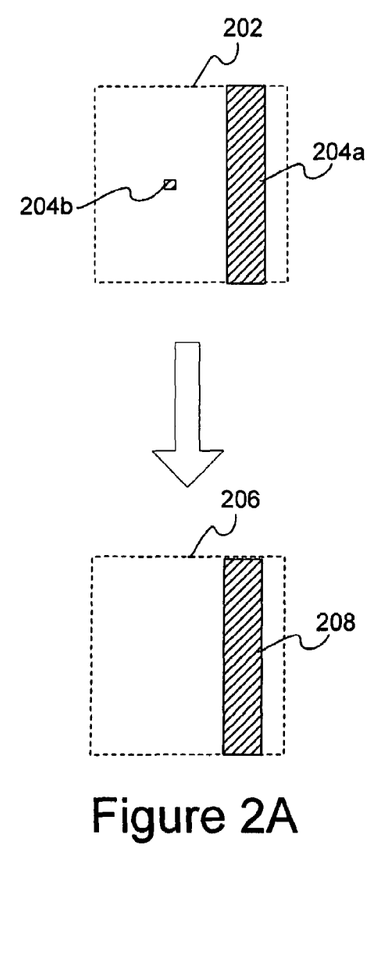
FIGS. 2A through 2C illustrate different types of reticle errors and how they affect the pattern printed on the wafer by the photolithography system.
Figure 2B:
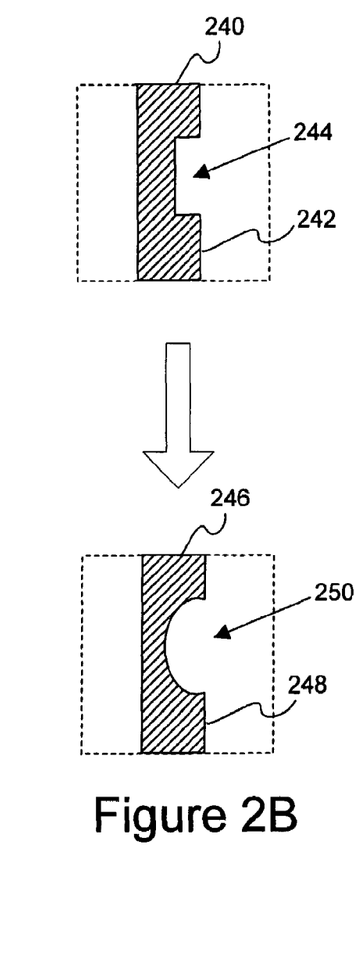
Figure 2C:
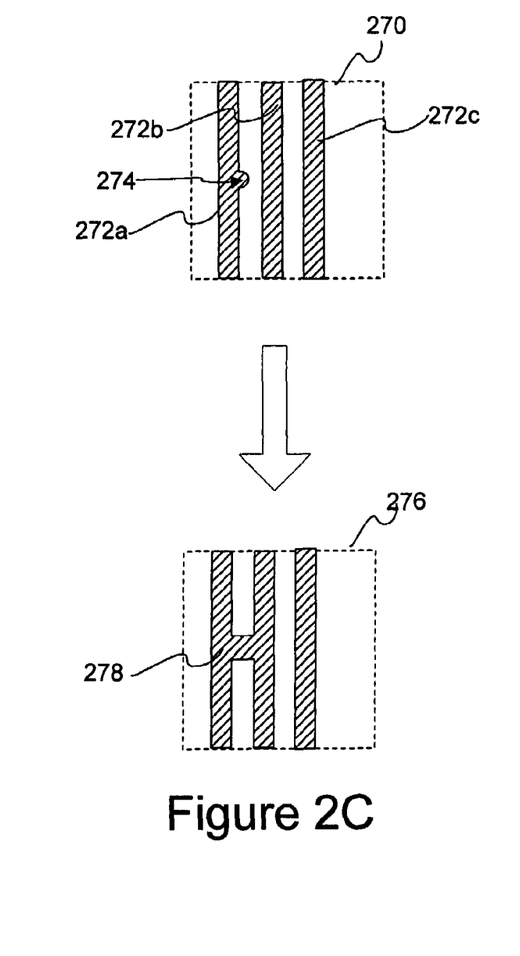

FIGS. 2A through 2C illustrate different types of reticle errors and how they affect the pattern printed on the wafer by the photolithography system. As shown in FIG. 2A, reticle 202 includes a line portion 204a and a small particular type defect 204b. When the defect is small compared to nearby design pattern structure or spaced far away from the design pattern structure of a reticle 202, the reticle defect is not printed on the wafer. As shown, the corresponding wafer portion 206 only contains a corresponding line 208 for reticle line portion 204a.

FIG. 2B illustrates a reticle having a line portion 242 with a partial open defect 244. In contrast to the defect of FIG. 2A, the reticle defect 244 of FIG. 2B is printed onto the wafer portion 246. As shown, the wafer portion 246 includes a corresponding line portion 248 containing a partial open defect 250. FIG. 2C illustrates a reticle 270 having a small defect 274 within a dense pattern of design line portions 272a through 272c. In this case, the small defect 274 results in a large defect 278 within the wafer portion 276.

In general terms, the present invention provides selective sensitivity in inspection of semiconductor specimens so that areas of the specimen which are more susceptible to defects are inspected with a higher inspection sensitivity than areas which have a lower defect susceptibility. In one embodiment, a reticle having a plurality of pattern portions is analyzed to thereby determine a characteristic of defect susceptibility for each pattern portion. One example of a characteristic of defect susceptibility is often referred to as mask error enhancement factor (MEEF). The defect susceptibility characteristic determined for each pattern portion is then used to select a sensitivity level for inspecting each reticle portion or its corresponding integrated circuit portion. Each portion of the reticle may then be inspected using the selected sensitivity level for the each reticle portion. By way of example, portions of the reticle that have been characterized as being more susceptible to defects on the corresponding integrated circuit portion are inspected with a more stringent threshold, while portions that have been characterized as being less or not susceptible to defects on the corresponding integrated circuit portion are inspected with a less stringent threshold. The defect susceptibility characteristic may also be used to selectively provide sensitivity levels for inspection of the resulting integrated circuit pattern portions.

Figure 3:
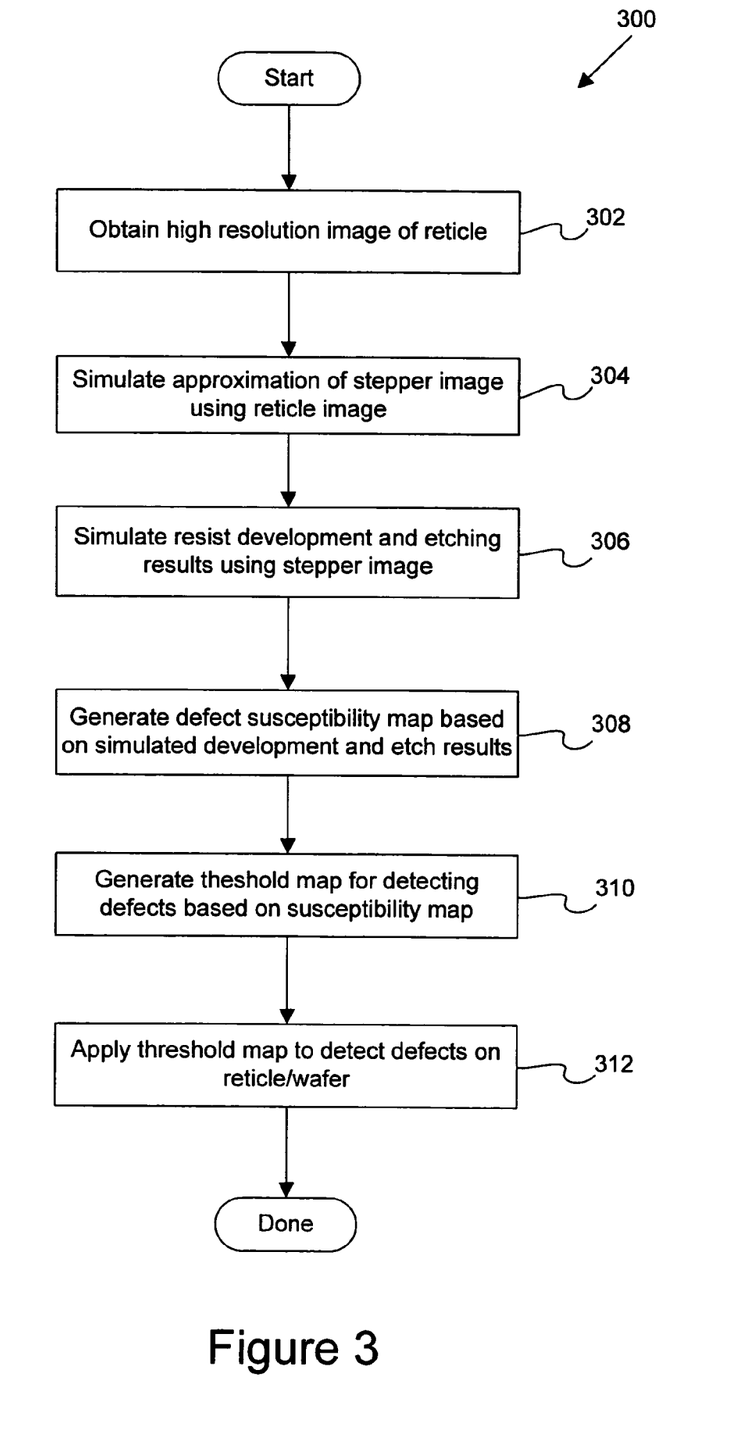
FIG. 3 is a flowchart illustrating a procedure for providing selected defect sensitivity in accordance with one embodiment of the present invention.

FIG. 3 is a flowchart illustrating a procedure 300 for providing selected defect sensitivity in accordance with one embodiment of the present invention. Initially, a high resolution image of the reticle is obtained in operation 302. The image of the reticle may be obtained with any suitable inspection or review tool. The tool may take the form of an optical system, such as a bright field or dark field optical system. The tool may also utilize both bright field and dark field modes. Examples of bright field systems include the 2350, 2351, 2360, and 2370 from KLA-Tencor, Corp. of San Jose, Calif. Examples of dark field system include the AIT II, AIT XP, Fusion, Fusion UV, and SP1 PatternPro available from KLA-Tencor, Corp. of San Jose, Calif. The reticle may also be imaged using any of the following other types of imaging systems, such as an electron beam imaging system.

Although the illustrated embodiment is described as being applied to the reticle image, the techniques of the present invention are preferably applied in parallel to both a test and baseline (or reference) image.

An approximation of the lithography image is then simulated using the reticle image in operation 304. In other words, operation 304 includes simulating an approximation of what the lithography image would look like after the reticle image is passed through the lithography optics. Certain properties of the lithography tool distort or alter the reticle image, resulting in an altered lithography image. By way of examples, the lithography tool reduces the overall size of the reticle image (e.g., by a factor of 4), rounds reticle feature corners or softens the edges of features. These alterations are approximated and used to simulate the lithography image based on the reticle image and the approximated alterations. Said in another way, the lithography tool projects or generates exposure patterns (e.g., 103c of FIG. 1) on the wafer based on a reticle image (e.g., 203b of FIG. 1) resulting from a light source beam (e.g., 203a of FIG. 1) being passed through the reticle.

The simulated lithography image also preferably incorporates some of the differences between the lithography tool image and the image produced by the inspection tool. Since an inspection system typically has a higher resolution than a lithography tool, the reticle image is preferably passed through a suitable low pass filter to simulate the lithography tool's lower resolution, as well as other imaging effects of the lithography tool. The filter may be implemented using any combination of hardware and/or software. Of course, the specifications of such a filter depends on the particular configuration (e.g., sigma, focus, illumination, wavelength, etc.) of the lithography tool.

The resist development results are then simulated using the lithography image in operation 306. Resist development includes exposing and then etching the photoresist material to thereby form a resist pattern. After resist development, the patterned photoresist is then typically used to form patterns in the underlying semiconductor layer by any suitable fabrication operation, such as an etching process, ion implantation, deposition, etc. The resist development simulation operation is also herein referred to as a "remapping" operation. Given the simulated lithography image, the resulting photoresist pattern and corresponding integrated circuit pattern are simulated. In other words, it is determined what portions of the lithography image will result in patterns being present or absent on the etched photoresist and underlying active layer pattern.

In operation 304, a defect susceptibility map is then generated based on the simulated development and etch results or the image generated from the remapping operation. The defect susceptibility map generally quantifies or characterizes the impact of a defect on each portion of the reticle. Certain defects depending on where they are located with respect to the reticle pattern have a larger or lower impact on the resulting wafer pattern. For instance, a particle defect will tend to have a more destructive impact when it falls within a relatively densely packed pattern area, as compared to a less dense pattern area. In a specific example, each reticle portion is associated with a pseudo-MEEF value, as further described below. A low MEEF value generally means that the corresponding reticle area is less susceptible to resulting in defects on the corresponding patterned wafer area, while a high MEEF value indicates a higher susceptibility to defects.

After a defect susceptibility map is generated for the various portions of the reticle, a threshold map is then generated for detecting defects based on the susceptibility map in operation 310. For instance, reticle portions which have low defect susceptibility are given a less sensitive or higher threshold value to be used during inspection, while reticle portions which have a high defect susceptibility are given a higher sensitivity or lower threshold value. Alternatively, a threshold map may be generated for inspection of each portion of the resulting integrated circuit based on the relative defect susceptibility values of the corresponding reticle portions.

The techniques of the present invention may be applied to either or both of a test or a reference image of a reticle. When the reference image is obtained from a design database, the reference image is preferably used. When the reference image is obtained from a portion of a reticle, the techniques of the present invention may be applied either the reference or test image to speed up the process. Alternatively, the techniques may be applied to both the reference and test image so that a defect susceptibility map is obtained for both the test and the reference image. Preferably, the most conservative results (e.g., the map which indicates a higher susceptibility) is then utilized for selecting defect detection sensitivity. Alternatively, the results (e.g., susceptibility maps) may be averaged together.

When both images are analyzed to obtain a susceptibility map, it may also be determined whether one of the images and corresponding reticle portions are significantly out of specification. When the test image's defect susceptibility map significantly differs from the baseline's susceptibility map, it may be determined that the reticle is out of specification. The reticle may the be reworked or discarded. The cause of such deviation may also be analyzed to prevent future discrepancies or adjust an out of specification reticle fabrication process.

The threshold map is then applied to detect defects on the reticle or wafer in operation 312. A test image of the reticle is typically compared to a baseline image. Typically, the baseline image is either generated from the circuit pattern data or from an adjacent die on the reticle itself. Either way, the test image features are analyzed and compared with corresponding features of the baseline image. Each difference value of each test image portion and its corresponding baseline image portion is then compared with the selected threshold value for these portions. If the test image feature varies from the baseline feature by more than the selected threshold, a defect is defined and an error is reported. The defect may be later reviewed to determine the significance of the defect (e.g., whether the defect will result in a fault on the integrated circuit). Preferably, a high resolution test image is compared to a high resolution baseline image, and a low resolution test image is compared to a low resolution baseline image. The high resolution images are obtained from the reticle itself, while the low resolution images are obtained after the operations 304 and 306 for simulating the lithography image and resist development results are applied to the high resolution reticle images. The threshold map is preferably applied to both comparisons to detect defects.

The test image and baseline image used in the above analysis may each be obtained from adjacent portions of the same reticle which are designed to be identical. Typically, a reticle includes a plurality of die patterns. Accordingly, a test image may be obtained from a first one of the dies of the reticle, while a baseline image may be obtained from a second one of the dies of the reticle.

Figure 4A:
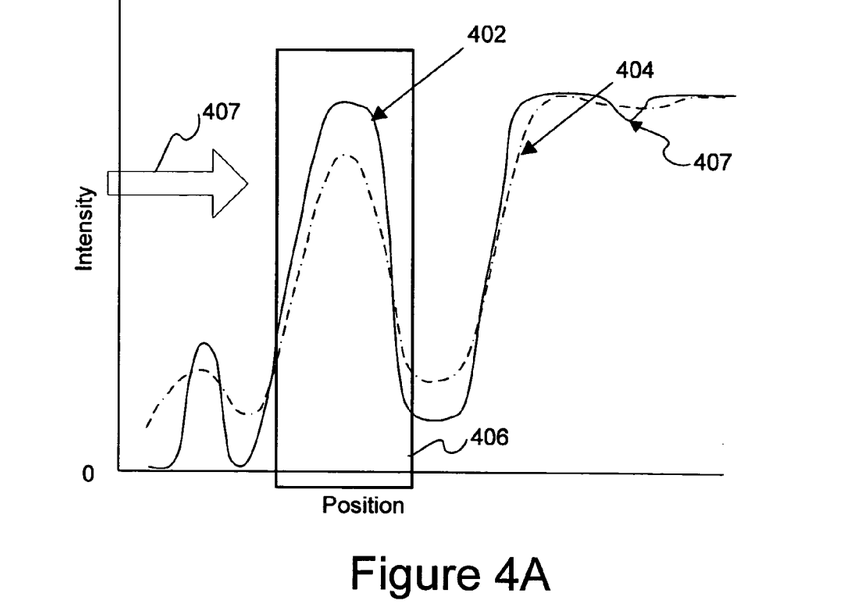
FIGS. 4A through 4B illustrate a procedure for simulating a lithography image based on a reticle image in accordance with one embodiment of the present invention.
Figure 4B:
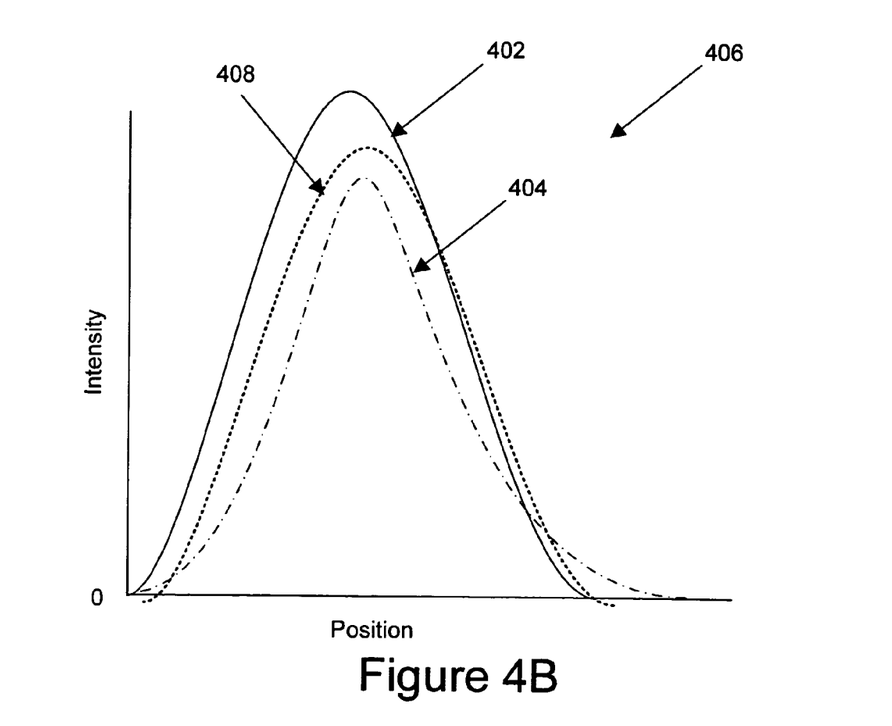

Any suitable procedure may be used to simulate an approximation of the lithography image. FIGS. 4A through 4B illustrate a procedure for simulating a lithography image based on a reticle image in accordance with one embodiment of the present invention. FIG. 4A is a graph of image intensity versus position on the image. The graph includes a reticle image curve 402 and the corresponding simulated lithography image curve 404 which is based on the reticle image 402.

In general terms, the reticle image signal 402 is converted into a corresponding lithography image, one window or kernel 406 at a time, e.g., in direction 407. In other words, the window 406 is sequentially stepped across the reticle image signal. For each window position, the reticle image signal 402 is convoluted with a filter function to thereby obtain the simulated lithography image signal 404. As shown in FIG. 4B, the window portion of reticle image signal 402 is convoluted with filter signal 408 to obtain a window portion for lithography image signal 404. The filter function for a particular photolithography tool may be obtained experimentally or by simulating/modeling the characteristics of the lithography tool. Generally, the filter is configured to "smooth out" (or reduce/eliminate the high frequency variations from the reticle signal) and reduce the values of the reticle image signal.

Figure 5A:
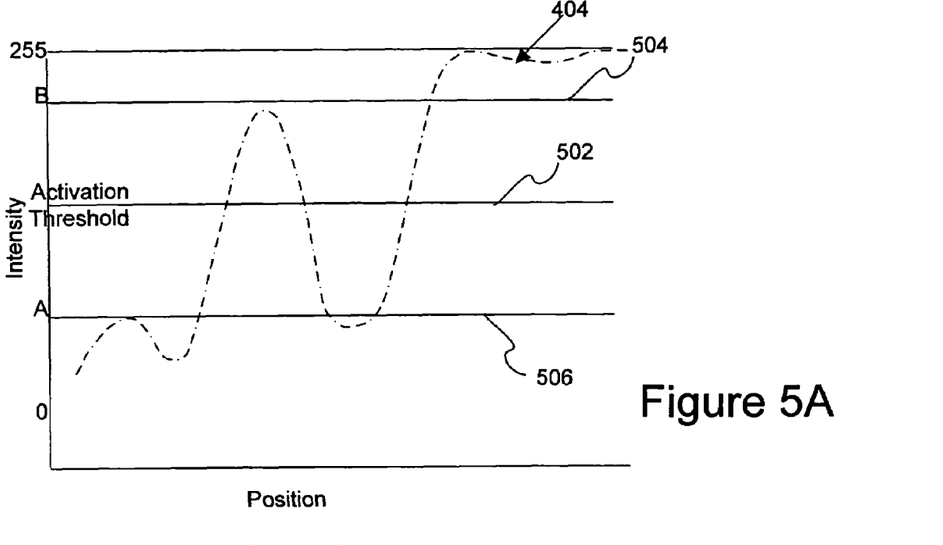
FIGS. 5A-5C illustrate a procedure for simulating resist development results in accordance with one embodiment of the present invention.
Figure 5B:
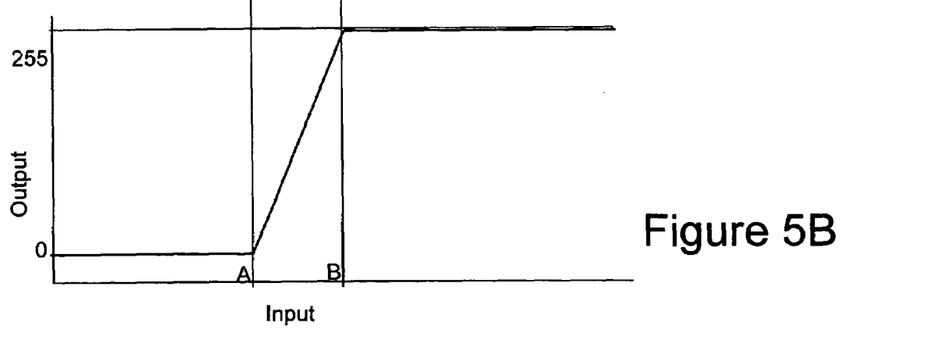
Figure 5C:
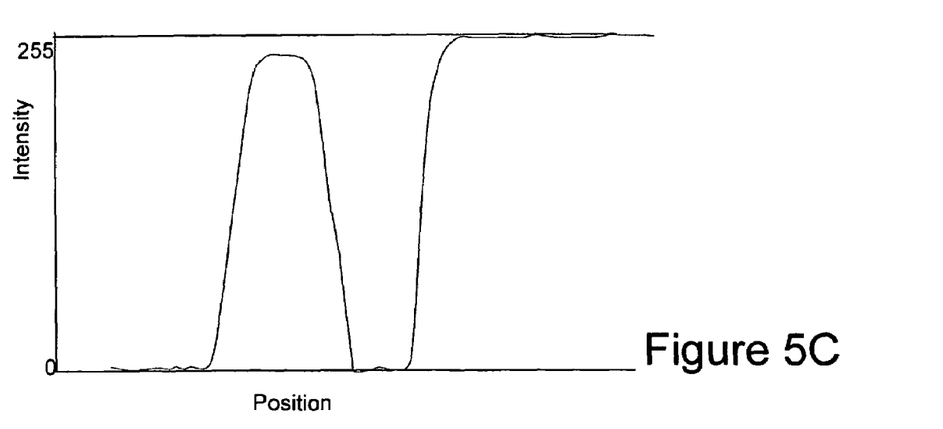

The resist development results may than be simulated in any suitable manner based on the lithography image. For example, a look-up table may be utilized to match lithography image values to activation outputs. FIGS. 5A-5C illustrate a procedure for simulating resist development results in accordance with one embodiment of the present invention. FIG. 5A is a graph of lithography image intensity as a function of image position. The activation threshold 502 for a particular lithography tool is shown as 502. When the photoresist is exposed to an intensity value above or equal to the activation threshold, it is activated. Intensity values below this threshold do not activate the photoresist. Of course the activation threshold varies with different photoresist materials and thickness levels, etc.

A user or operator selects a threshold B value 504 at which intensity values above such threshold are fully activated to maximum intensity. A user or operator also selected a second threshold A 506 below which there is zero activation. Of course, thresholds A and B may also be selected automatically without an operator or user. Intensity values that are between A and B result in varying degrees of activation. FIG. 5B illustrates one example of activation output as a function of intensity input. As shown, intensity values above threshold B result in a maximum intensity value of 255. Intensity input values below threshold A result in an activation output value of zero. Although the intensity values are chosen to be in the range of 0~255, of course, other intensity ranges may be utilized and depend on the particular requirements of the application. FIG. 5C illustrates a remapping of the lithography image based on the activation threshold in accordance with one embodiment of the present invention.

The activation threshold depends on the resist material characteristics. Thresholds A and B are selected to capture defects of interest. For instance, defects which result in an intensity above threshold A and below threshold B do not typically produce defects on the wafer. So these defects are smoothed out of the resulting exposure graph (e.g., FIG. 5C). Other factors which affect selection of thresholds A and B include noise in the reticle image.

The susceptibility characteristics of each reticle portion may then be determined based on the simulated resist development and etching or remapping results in any suitable manner. In general, rules may be defined for determining whether to give each reticle portion a higher or lower relative susceptibility value based on the corresponding remapping results for such reticle portion. In one embodiment, the results from two rules are followed:

1. When the slope of the remapping results are relatively steep, a lower susceptibility value is used, and when the slope is shallower, a higher susceptibility value is used; and 2. When a remapping result value is relatively far away from the activation threshold, a lower susceptibility value is used, and when a remapping result value is relatively close to the activation threshold, a lower susceptibility value is used.

Figure 6A:
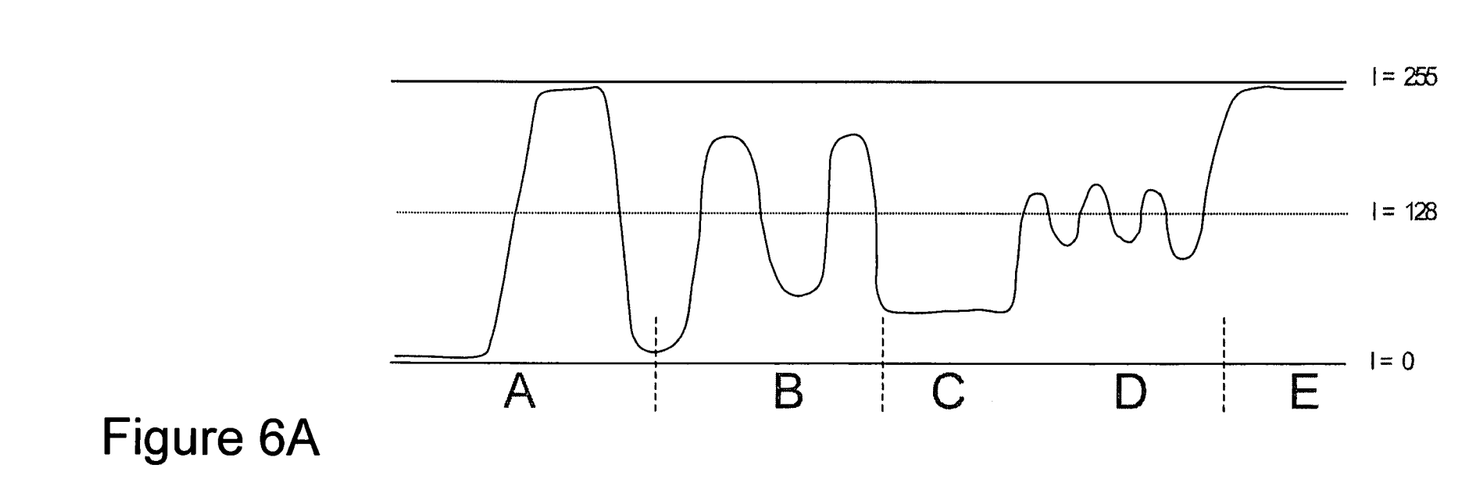
FIG. 6A illustrates an example resist development and etch graph of intensity as a function of position as produced by the techniques of the present invention.

FIG. 6A illustrates an example remapping graph of intensity as a function of position as produced by the techniques of the present invention. As shown, section A has a gradually sloped intensity peak corresponding to a relatively large feature, and section B has two gradually sloped intensity peaks corresponding to higher density features than the peak of section A. Section C has a flat intensity portion; while section D has a relatively high frequency portion which corresponds to dense features. Section E corresponds to another large structure.

Figure 6B:
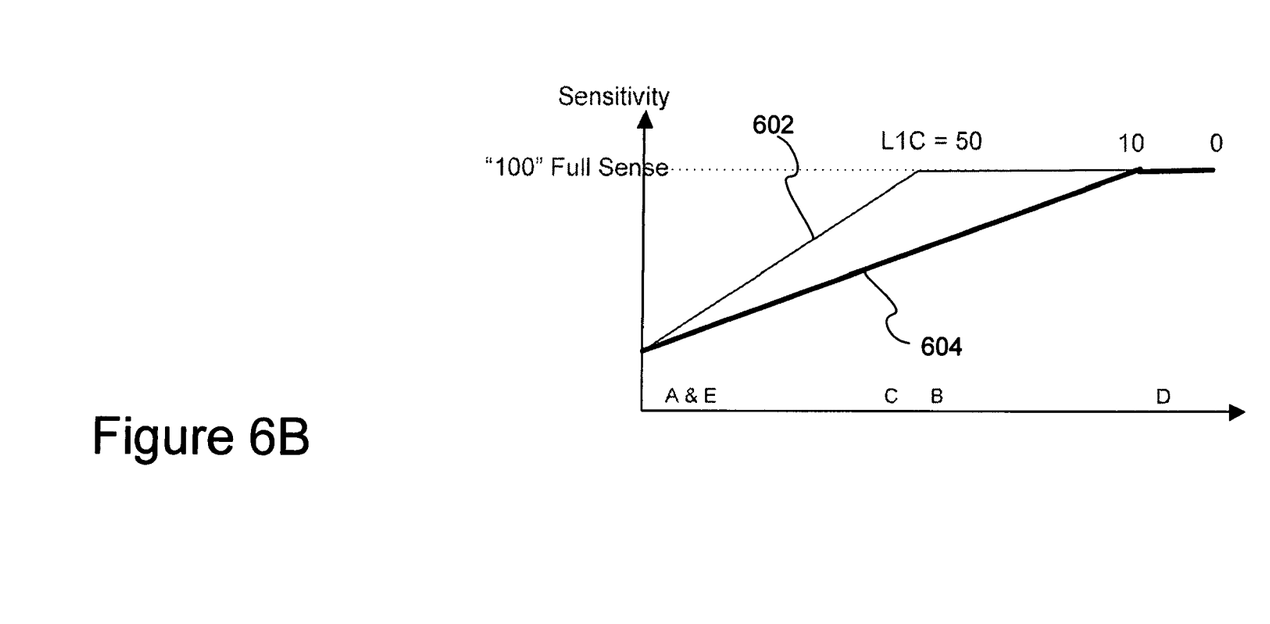
FIG. 6B illustrates a technique for determining defect susceptibility (e.g., MEEF) based on the resist development results of FIG. 6A in accordance with one embodiment of the present invention.

FIG. 6B illustrates a technique for determining defect susceptibility based on the resist development results of FIG. 6A in accordance with one embodiment of the present invention. In this embodiment, the susceptibility is defined as a pseudo-MEEF (Mask Error Enhancement Factor). In the illustrated embodiment, MEEF is shown as a function of resist development and etch result areas A through E. The MEEF is determined as a function of the slope and distance from the activation threshold for each resist development and etch result area. The determination of MEEF may be selectable. A first MEEF graph 602 and a second MEEF graph 604 are shown in FIG. 6B, which graphs are both obtained from applying a function to the results of FIG. 6A.

In general, the MEEF calculation will determine the sensitivity of the inspection. A "100" value is shown as a maximum MEEF or maximum detection sensitivity although this value is arbitrary. As shown for both MEEF graphs 602 and 604, sensitivity is highest for areas D and lowest for areas A and E. The variable L1C controls the location of the breakpoint for the transition from maximum sensitivity to decreasing sensitivity. The minimum sensitivity is usually applied to large objects with a simple geometry, while the maximum sensitivity are applied to exposure intensities which are proximate to the activation threshold. The activation threshold in this illustrated embodiment is 128 (shown in FIG. 6A). For MEEF graph 602, an L1C of 50 results in a maximum sensitivity for area B, while an L1C of 10 results in a decreased sensitivity for area B. Of course, the specific algorithm used for calculating MEEF and adjusting the MEEF value (e.g., L1C) depends on the particular level of sensitivity and accuracy desired from the results of the inspection.

The threshold for a particular area may then be generally determined by:

$$T = c + kM$$

where M is the susceptibility value for such area and c and k are constants. The constants c and k depend on the noise in the image. For instance, constant c is set low when noise is low, and set high when noise is high. Both constants c and k also depend on the level of desired or tolerated sensitivity, weighed against the likelihood of capturing false defects when the threshold is set too low. Thus, when there is a significant amount of noise, c and k are set to produce a higher threshold value, and visa versa. Example equations with suitable constants for determining threshold are further described below.

In more specific implementation, MEEF is also defined as 1/NILS, where NILS stands for Normalized Image Log Slope (e.g., of the lithography image. That is, the steeper the local slope in the lithography image, the smaller MEEF is. One may determine NILS from the lithography image using a few simplifications. For instance, NILS is approximated as simply the grayscale gradient in the lithography image. Preferably NILS is only calculated using the baseline image and not the test image. There is a risk that an error in the baseline image may impact the NILS calculation unfavorably. However, in order to impact the NILS and resulting MEEF calculation, a defect has to be relatively large, and therefore even when this happens, it should not impact the detection of the large defect. Given these simplifications and assumptions, NILS may be determined by:

$$NILS = \frac{\sqrt{(I \otimes g_x)^2 + (I \otimes g_y)^2}}{G_{max}}$$

where I is the simulated lithography image and $g_x$ and $g_y$ are the same gradient filter oriented in the X and Y directions respectively. The following is an example of $g_x$:

$$g_x = [-14, -29, -28, 0, 28, 29, 14]/256$$

This value is roughly equivalent to the derivative of a Gaussian with sigma=1.5 pixel. The gradient filter is selected based on desired computational efficiency and the desired signal to noise ratio of the image. For instance, a larger filter results in more computational time. $G_{max}$ is the maximal possible gradient given the lithographic processing. $G_{max}$ is measured by lithographically processing an ideal isolated step edge and using the peak gradient as $G_{max}$.

If we use only the gradient as a measurement of local MEEF, the flat areas (all clear or opaque) can have large MEEF as well. However, lithographically, those areas do not matter much because they are far away from the resist threshold. To accommodate this observation, the overall threshold weight function may then be determined by:

$$w = \alpha \cdot NILS * 256 + \beta \cdot |I - 128| \cdot 2$$

where 128 is the resist threshold. Of course, the resist threshold will change with different resist materials and different intensity ranges used for the lithography or inspection system. Thus, the threshold weight depends on the distance from the resist threshold, where the distance is defined as the absolute value of the image intensity value minus the resist threshold (128 in this example). The threshold is now halfway in between the maximum intensity value 255 and the minimum intensity value of 0 due to the remapping operation. However, these values are arbitrary and depend on the configuration of the lithography and/or inspection system. The constants $\alpha = 1.0$ and $\beta$ depend on the desired level of sensitivity weighed against the tolerable level of detected false defects. In one implementation, $\alpha = 1.0$ and $\beta = 0.25$ work well. The threshold weight w is clipped at 255. However, this maximum intensity value is optional and varies with the implementation, e.g., it may depend on the number of bits used to store the intensity value.

The threshold may then be determined for individual reticle portions based on the susceptibility map and determined threshold weight function so that areas of low defect susceptibility have a higher threshold and areas of higher susceptibility have a lower threshold. Any suitable technique may be used to achieve this goal.

To allow adjustment of the threshold locally according to MEEF, the threshold may be determined by:

$$T_{meef} = T \cdot \left(1 + \frac{w}{256} \cdot \frac{c}{100}\right)$$

where c is a user defined variable that allows adjustment of MEEF enhancement levels and T is a predetermined threshold. When c is set to 0, there is no MEEF enhancement and the threshold is set to predetermined threshold value T. The predetermined threshold may be determined by experimentation. When c is set to the maximal 100, the detection threshold at the lowest MEEF (i.e., high NILS and/or far away from resist development threshold) can be as much as twice the threshold at the high MEEF area. Of course, the threshold range is adjustable and varies with the particular requirements of the inspection.

The techniques of the present invention may be implemented in any suitable combination of software and/or hardware system. For example, the techniques may be implemented within an inspection tool. Preferably, an optical, electron beam, or other inspection system is integrated with a computer system which implements many of the method steps of this invention. Such composite system preferably includes at least (a) an imaging system arranged to generate an optical or electron beam image of the reticle, both a test and baseline image, and (b) a processing unit configured to compare the baseline and current test images and thereby identify defects. At a minimum, the imaging system will usually include (i) a source of illumination oriented to direct radiation onto a specified location of the reticle; and (ii) one or more detectors oriented to detect an image of the reticle from the source which has been scattered by the reticle. The imaging system may also include a scanning mechanism.

Regardless of the system's configuration, it may employ one or more memories or memory modules configured to store data, program instructions for the general-purpose inspection operations and/or the inventive techniques described herein. The program instructions may control the operation of an operating system and/or one or more applications, for example. The memory or memories may also be configured to store layout patterns, layout constraint rules and target rules.

Because such information and program instructions may be employed to implement the systems/methods described herein, the present invention relates to machine readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave traveling over an appropriate medium such as airwaves, optical lines, electric lines, etc. Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. A method of providing selective defect sensitivity in inspection of semiconductor reticles, the method comprising:
   a) providing a target portion of a reticle, wherein the target portion comprises a plurality of pattern portions;
   b) analyzing the pattern portions of the reticle to thereby determine a characteristic of defect susceptibility for each pattern portion, wherein each characteristic of defect susceptibility is a quantification of the predicted impact of a defect in the corresponding pattern portion of the reticle on a corresponding portion of a wafer that is to be fabricated with such each pattern portion of the reticle;
   c) determining and storing a sensitivity level for inspection of each pattern portion of the reticle that corresponds to the determined defect susceptibility characteristic of such each pattern portion; and
   d) inspecting each portion of the reticle using the determined sensitivity level for such reticle portion,
   wherein the operation of analyzing the pattern portions of the reticle comprises:
      simulating an approximation of a lithography image which would be produced by a lithography tool which is to be used to expose a semiconductor device with the reticle;
      simulating resist development results using the approximation of the lithography image; and
      generating the sensitivity levels in the form of a defect susceptibility map for the reticle based on the simulated resist development results,
      wherein the approximation of the lithography image is simulated by convoluting a low pass filter function with an image of the target portion of the reticle and wherein the low pass filter function also incorporates at least some of the differences between the lithography tool and an inspection tool which is to be used to inspect the reticle or a semiconductor device fabricated from such reticle.

2. A method as recited in claim 1, further comprising inspecting each portion of the reticle using the determined sensitivity level for such reticle portion.

3. A method as recited in claim 1, wherein the determination of the sensitivity level for each pattern portion includes selecting a threshold for each pattern portion based on the determined defect susceptibility characteristic of such pattern portion.

4. A method as recited in claim 3, further comprising inspecting each portion of the reticle by comparing the each portion with a corresponding baseline portion to obtain a difference value and determining that the each portion contains a defect if the difference value is greater than the selected threshold for such reticle portion.

5. A method as recited in claim 1, further comprising inspecting a plurality of wafer portions fabricating with corresponding pattern portions of the reticle, wherein inspection of each wafer portion is based on the determined defect susceptibility characteristic for the corresponding pattern portion of the reticle.

6. A method as recited in claim 1, wherein the inspection is a reticle inspection performed with a reticle inspection system.

7. A method as recited in claim 6, wherein the reticle inspection system is either a brightfield or a darkfield optical system.

8. A method as recited in claim 1, further comprising performing operations (a) through (c) for both a target portion of the reticle and a baseline portion of the reticle, wherein the target portion is designed to be substantially identical to the baseline portion of the reticle, wherein the sensitivity level for the inspection is based on the defect susceptibility of the target portion or the reference portion which has the highest defect susceptibility.

9. A method as recited in claim 8, further comprising:
   determining whether the characteristics of defect susceptibility for the target portion significantly differs from the characteristics of defect susceptibility for the baseline portion; and
   when the characteristics of defect susceptibility for the target portion significantly differs from the characteristics of defect susceptibility for the baseline portion, determining that the reticle is out of specification and halting processing of such reticle.

10. A method as recited in claim 9, further comprising reworking the reticle to repair damage to the reticle when it is determined that the reticle is out of specification.

11. A method as recited in claim 9, further comprising determining a cause of the out of specification when it is determined that the reticle is out of specification.

12. A method as recited in claim 1, wherein the low pass filter function is further based on at least a portion of a plurality of configuration parameters associated with the lithography tool.

13. A method as recited in claim 1, wherein the defect susceptibility map is in the form of a pseudo Mask Error Enhancement Factor (MEEF) map and wherein the sensitivity level for inspection is in the form of threshold map specifying a plurality of threshold values, wherein high MEEF values result in low threshold values and low MEEF values result in high threshold values.

14. A method as recited in claim 1, further comprising:
   in a first comparison, comparing an image of the target portion to an image of an baseline portion of the reticle and determining that the target portion has a defect based on the comparison and determined sensitivity levels, wherein the target portion is designed to be substantially identical to the baseline portion of the reticle; and
   in a second comparison, comparing the resist development results obtained from the image of the target portion to the resist development results obtained from the image of the baseline portion and determining that the target portion has a defect based on the second comparison and the determined sensitivity levels.

15. A method as recited in claim 14, wherein the sensitivity levels are inspection threshold values.

16. A method as recited in claim 1, wherein generating the defect susceptibility map is accomplished by combining results from the following rules:
   when a slope of the simulated resist development results is relatively steep, associating a higher defect susceptibility value to the corresponding reticle portion;

when a slope of the simulated resist development results is relatively shallow, associating a lower defect susceptibility value to the corresponding reticle portion;

when an intensity value of the simulated resist development results is a relatively far distance from an activation threshold of a resist material which is to be used with the reticle, associating a lower defect susceptibility value to the corresponding reticle portion; and when an intensity value of the simulated resist development results is a relatively short distance from an activation threshold of a resist material which is to be used with the reticle, associating a higher defect susceptibility value to the corresponding reticle portion.

17. A method as recited in claim 1, wherein the defect characteristics for the pattern portions are based on a pseudo Mask Error Enhancement Factor (MEEF) map.

18. A computer system operable to provide selective defect sensitivity in inspection of semiconductor reticles, the computer system comprising:

one or more processors;

one or more memory, wherein at least one of the processors and memory are adapted for:

a) providing a target portion of a reticle, wherein the target portion comprises a plurality of pattern portions;

b) analyzing the pattern portions of the reticle to thereby determine a characteristic of defect susceptibility for each pattern portion, wherein each characteristic of defect susceptibility is a quantification of the predicted impact of a defect in the corresponding pattern portion of the reticle on a corresponding portion of a wafer that is to be fabricated with such each pattern portion of the reticle;

c) determining and storing a sensitivity level for inspection of each pattern portion of the reticle that corresponds to the determined defect susceptibility characteristic of such each pattern portion; and d) inspecting each portion of the reticle using the determined sensitivity level for such reticle portion, wherein the operation of analyzing the pattern portions of the reticle comprises:

simulating an approximation of a lithography image which would be produced by a lithography tool which is to be used to expose a semiconductor device with the reticle;

simulating resist development results using the approximation of the lithography image; and generating the sensitivity levels in the form of a defect susceptibility map for the reticle based on the simulated resist development results wherein the approximation of the lithography image is simulated by convoluting a low pass filter function with an image of the target portion of the reticle and wherein the low pass filter function also incorporates at least some of the differences between the lithography tool and an inspection tool which is to be used to inspect the reticle or a semiconductor device fabricated from such reticle.

19. A computer system as recited in claim 18, wherein the at least one of the processors and memory are further adapted for inspecting each portion of the reticle using the determined sensitivity level for such reticle portion.

20. A computer system as recited in claim 18, wherein the determination of the sensitivity level for each pattern portion includes selecting a threshold for each pattern portion based on the determined defect susceptibility characteristic of such pattern portion.

21. A computer system as recited in claim 20, wherein the at least one of the processors and memory are further adapted for inspecting each portion of the reticle using the selected threshold for such reticle portion.

22. A computer system as recited in claim 18, wherein the at least one of the processors and memory are further adapted for inspecting a plurality of wafer portions fabricating with corresponding pattern portions of the reticle, wherein inspection of each wafer portion is based on the determined defect susceptibility characteristic for the corresponding pattern portion of the reticle.

23. A computer system as recited in claim 18, wherein the inspection is a reticle inspection performed with a reticle inspection system.

24. A computer system as recited in claim 23, wherein the reticle inspection system is either a brightfield or a darkfield optical system.

25. A computer system as recited in claim 18, wherein the at least one of the processors and memory are further adapted for performing operations (a) through (c) for both a target portion of the reticle and a baseline portion of the reticle, wherein the target portion is designed to be substantially identical to the baseline portion of the reticle, wherein the sensitivity level for the inspection is based on the defect susceptibility of the target portion or the reference portion which has the highest defect susceptibility.

26. A computer system as recited in claim 25, wherein the at least one of the processors and memory are further adapted for:

determining whether the characteristics of defect susceptibility for the target portion significantly differs from the characteristics of defect susceptibility for the baseline portion; and when the characteristics of defect susceptibility for the target portion significantly differs from the characteristics of defect susceptibility for the baseline portion, determining that the reticle is out of specification and halting processing of such reticle.

27. A computer system as recited in claim 26, wherein the at least one of the processors and memory are further adapted for reworking the reticle to repair damage to the reticle when it is determined that the reticle is out of specification.

28. A computer system as recited in claim 26, wherein the at least one of the processors and memory are further adapted for determining a cause of the out of specification when it is determined that the reticle is out of specification.

29. A computer system as recited in claim 18, wherein the defect susceptibility map is in the form of a pseudo Mask Error Enhancement Factor (MEEF) map and wherein the sensitivity level for inspection is in the form of threshold map specifying a plurality of threshold values, wherein high MEEF values result in low threshold values and low MEEF values result in high threshold values.

30. A computer system as recited in claim 18, wherein the at least one of the processors and memory are further adapted for:

in a first comparison, comparing an image of the target portion to an image of an baseline portion of the reticle and determining that the target portion has a defect based on the comparison and determined sensitivity levels, wherein the target portion is designed to be substantially identical to the baseline portion of the reticle; and in a second comparison, comparing the resist development results obtained from the image of the target portion to the resist development results obtained from the image of the baseline portion and determining that the target portion has a defect based on the second comparison and the determined sensitivity levels.

31. A computer system as recited in claim 30, wherein the sensitivity levels are inspection threshold values.

32. A computer system as recited in claim 18, wherein generating the defect susceptibility map is accomplished by combining results from the following rules:
when a slope of the simulated resist development results is relatively steep, associating a higher defect susceptibility value to the corresponding reticle portion;
when a slope of the simulated resist development results is relatively shallow, associating a lower defect susceptibility value to the corresponding reticle portion;
when an intensity value of the simulated resist development results is a relatively far distance from an activation threshold of a resist material which is to be used with the reticle, associating a lower defect susceptibility value to the corresponding reticle portion; and
when an intensity value of the simulated resist development results is a relatively short distance from an activation threshold of a resist material which is to be used with the reticle, associating a higher defect susceptibility value to the corresponding reticle portion.

33. A computer system as recited in claim 18, wherein the defect characteristics for the pattern portions are based on a pseudo Mask Error Enhancement Factor (MEEF) map.

* * * * *